(12) United States Patent
Myers

(10) Patent No.: US 12,735,373 B2
(45) Date of Patent: Sep. 15, 2026

(54) METHOD FOR TREATING A HEAVY BYPRODUCT STREAM FROM CHLORINATED PROPANE PRODUCTION

(71) Applicant: BLUE CUBE IP LLC, Clayton, MO (US)

(72) Inventor: John D. Myers, Clayton, MO (US)

(73) Assignee: BLUE CUBE IP LLC, St. Louis, MO (US)

( * ) Notice: Subject to any disclaimer, the term of this patent is extended or adjusted under 35 U.S.C. 154(b) by 592 days.

(21) Appl. No.: 18/254,679

(22) PCT Filed: Sep. 29, 2021

(86) PCT No.: PCT/US2021/052638
§ 371 (c)(1),
(2) Date: May 26, 2023

(87) PCT Pub. No.: WO2022/115151
PCT Pub. Date: Jun. 2, 2022

(65) Prior Publication Data

US 2024/0018073 A1 Jan. 18, 2024

Related U.S. Application Data

(60) Provisional application No. 63/119,434, filed on Nov. 30, 2020.

(51) Int. Cl.
*C07C 17/25* (2006.01)
*C07C 17/275* (2006.01)

(52) U.S. Cl.
CPC ............ *C07C 17/25* (2013.01); *C07C 17/275* (2013.01)

(58) Field of Classification Search
CPC ..... C07C 17/25; C07C 17/275; C07C 17/278; C07C 19/01; C07C 21/04
See application file for complete search history.

(56) References Cited

U.S. PATENT DOCUMENTS 9,321,707 B2 4/2016 Tirtowidjojo et al.
9,896,400 B2 2/2018 Filas et al.
(Continued)

FOREIGN PATENT DOCUMENTS

WO 2014046970 A1 3/2014
WO 2016058569 A9 6/2016
(Continued)

OTHER PUBLICATIONS

Extended European Search Report for EP Application No. 21898870.7, dated Oct. 14, 2024, 10 pages.
(Continued)

*Primary Examiner* — Jafar F Parsa
(74) *Attorney, Agent, or Firm* — Husch Blackwell LLP

(57) ABSTRACT

A process for treating a heavy byproduct stream from an initial chlorinated propane forming reaction in order to increase the final output of chlorinated propene and remove metal catalyst. In particular, the process disclosed herein provides for a primary stream in which chlorinated propanes are converted to chlorinated propenes in a catalytic dehydrochlorination reaction, while also treating a separate byproduct stream with a caustic to precipitate metal from a metal catalyst and convert any remaining chlorinated propanes to chlorinated propenes in order to increase final chlorinated propene output.

32 Claims, 2 Drawing Sheets

(56) References Cited

U.S. PATENT DOCUMENTS

| | | | |
|---|---|---|---|
| 2014/0221705 | A1 | 8/2014 | Wang et al. |
| 2017/0226034 | A1 | 8/2017 | Sherwood et al. |
| 2018/0265438 | A1 | 9/2018 | Wilson et al. |
| 2019/0202759 | A1 | 7/2019 | Myers et al. |

FOREIGN PATENT DOCUMENTS

| | | | |
|---|---|---|---|
| WO | 2019195247 | A1 | 10/2019 |
| WO | 2019195248 | A1 | 10/2019 |

OTHER PUBLICATIONS

International Search Report and Written Opinion for PCT/US2021/052638 mailed Jan. 18, 2022 (Applicant—Blue Cube IP LLC) (11 Pages).

METHOD FOR TREATING A HEAVY BYPRODUCT STREAM FROM CHLORINATED PROPANE PRODUCTION

CROSS REFERENCE

This application is a national phase application of PCT Application No. PCT/US2021/052638 filed Sep. 29, 2021, which claims benefit of priority to U.S. Provisional Patent Application Ser. No. 63/119,434, filed Nov. 30, 2020, which are herein incorporated by reference in their entirety.

FIELD OF THE INVENTION

The present disclosure generally relates a process for treating chloroalkane streams, and in particular for the treatment of byproduct streams and formation of chloroalkenes and.

BACKGROUND OF THE INVENTION

Chloroalkenes are useful intermediates for many products including agricultural products, refrigerants, pharmaceuticals, cleaning solvents, blowing agent, gums, silicons, and refrigerants. In order to form such chloroalkenes, generally an initial reaction is conducted for the formation of an intermediate product including chlorinated alkanes. These chloroalkanes are then subjected to a subsequent reaction to produce chloroalkenes.

The crude intermediate product from the initial reaction may include components other than the chloroalkanes including catalysts, heavy chlorinated byproducts as well as other compounds. Separation processes may be carried out with respect to the crude intermediate product in order to obtain a purified intermediate product, prior to the subsequent reaction for the formation of chloroalkenes. Various residual streams may be generated from these separations, and these may be recycled, further treated or disposed of.

BRIEF DESCRIPTION OF FIGURES

Implementations of the present technology will now be described, by way of example only, with reference to the attached figures, wherein.

DETAILED DESCRIPTION

Figure 1:
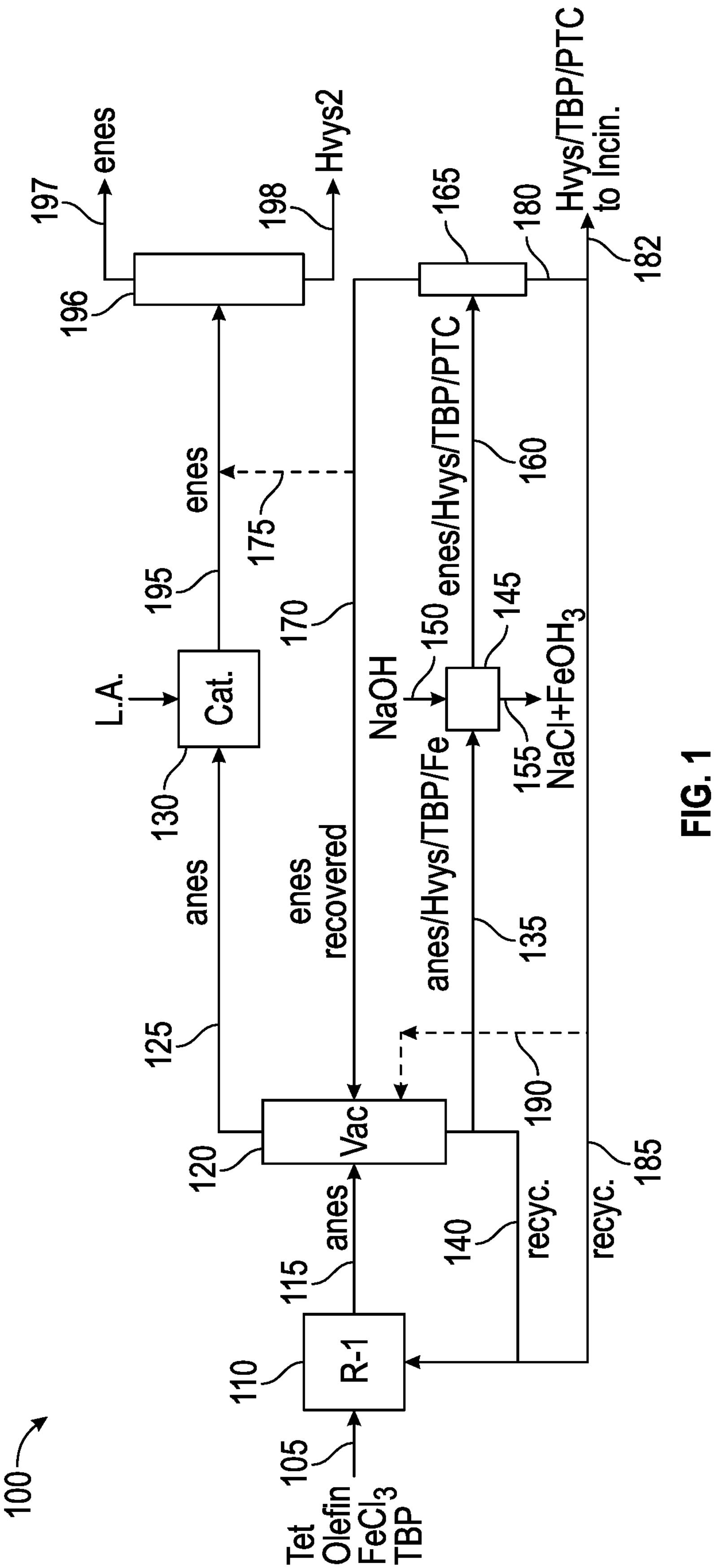
FIG. 1 is a schematic of one exemplary embodiment of a process for the caustic treatment of a heavy byproduct stream.

Various embodiments of the disclosure are discussed in detail below. While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, it may not be included or may be combined with other features.

(I) Introduction

Fluorocarbons are highly valuable compounds employed in a number of products, and most predominantly used as refrigerants. In the chemical pathway to the formation of fluorocarbons, a number of intermediate compounds are also prepared. These intermediate compounds are themselves valuable as well as the processes for their preparation in order to reduce the overall costs in the preparation of fluorocarbons. In order to reduce costs, more efficient and effective processes are sought for their formation. Such intermediate compounds include various chlorinated alkanes and chlorinated alkenes Disclosed herein is a process for treating a heavy byproduct stream from an initial chlorinated propane forming reaction in order to increase the final output of chlorinated propene and remove metal catalyst. In particular, the process disclosed herein provides for a primary or main stream in which chlorinated propanes are converted to chlorinated propenes in a catalytic dehydrochlorination reaction, while also treating a separate byproduct stream with a caustic to convert any remaining chlorinated propanes to chlorinated propenes in order to increase final chlorinated propene output.

An initial reaction is conducted via a telomerization to form chlorinated propanes. From this reaction, a crude chlorinated propane product is formed having a desired chlorinated propane intermediate and various heavy byproducts and residual reaction components. This crude chlorinated propane product is subject to a separation process to produce a light fraction having a purified chlorinated propane and a heavy fraction having the heavy byproducts and residual reaction components. The chlorinated propane in the light fraction may be further purified to remove components lighter than the chlorinated propane. Thus purified, the chlorinated propane is converted to chlorinated propenes using a Lewis catalyst in a dehydrochlorination reaction. The heavy fraction typically contains the chlorinated propane as well as byproducts heavier than the chlorinated propane, as well as other residual components from the initial reaction including a metal catalyst, promoter, complexes of the catalyst and promoter, or other reaction products.

Conventionally, this heavy byproduct stream may be considered a waste stream and may be fed to an incinerator for disposal or at least partially recycled to return catalyst components to the initial reaction. The problems associated with the heavy byproduct stream include that (1) the uncomplexed promoter in the stream is catalytically active when recycled to the initial chlorinated alkane producing step (e.g., telomerization step), whereas the metal catalyst-promoter complex is relatively inactive; (2) the metal content of the heavy byproduct stream makes it difficult to dispose of via incineration due to regulatory requirements; and (3) the heavy byproduct stream still contains a significant amount (30-70%) of useful chlorinated propane intermediate product, which represents a yield loss and increases the volume of the incineration stream, thereby increasing incineration cost.

However, as disclosed herein, this heavy byproduct stream is instead treated in order to achieve a multiplicity of positive results, including at least (1) removal of any metal catalyst from the stream, and (2) conversion of residual chlorinated propane to chlorinated propene. The treatment may include contacting the heavy fraction with a caustic, such as an aqueous base. This results in a precipitation reaction within the aqueous base causing precipitation of the metal from the metal catalyst, as well as a dehydrochlorination reaction in which the chlorinated propane is converted to chlorinated propenes. The contact of the aqueous base with the heavy fraction also forms two phases, an aqueous phase and an organic phase. The metal precipitates into the aqueous phase and the organic phase contains the chloropropane and/or chloropropene product and heavy byproducts. The aqueous phase can be separated from the organic phase and further treated to remove the precipitated metal. The organic phase may also be subjected to an additional separation to remove the chloropropene product, and/or recycled to the crude chloropropane product separation, wherein the chlorinated propene product will be distilled overhead along with the chlorinated propane intermediate product.

Benefits of the present disclosure include that the lower boiling point chlorinated propene products can be more easily recovered by distillation, or other separations operation, from the treated heavy byproduct stream and combined with the chlorinated propene products from the catalytic dehydrochlorination of the chloropropane by Lewis acid catalyst. An advantage results in that the overall yield to the desired chloropropene product(s) is increased, and the volume of the byproduct stream that must be incinerated is reduced, thereby reducing incineration cost.

Another improvement resulting from the present disclosure is that, since the chlorinated propane product remaining in the heavy byproduct stream is to be recovered as chlorinated propene by caustic dehydrochlorination treatment, the requirements for the crude chlorinated propane product separation, such as vacuum distillation, can be relaxed to allow more of the chlorinated propane product to remain in the heavy byproduct stream. Reducing the vacuum requirement of the distillation reduces the capital and operating costs, and reducing the temperature of distillation reduces the thermal decomposition of the promoter, which improves the effectiveness of promoter recycle and can prevent plugging issues in the chlorinated propane production reaction system (e.g., telomerization) caused by promoter decomposition products.

Another improvement resulting from the present disclosure is that the uncomplexed promoter contained in the treated heavy byproduct stream is more active in the initial telomerization reactor. A portion of the treated heavy byproduct stream may be recycled directly to initial reactor, or it may be recycled to the crude chloropropane product separation and then recycled to the initial reactor with a portion of the untreated heavy byproduct stream. In the latter case, the recycled promoter will comprise both complexed and uncomplexed promoter. In such embodiments, a larger amount of uncomplexed promoter will be recycled to the initial reactor than if only the untreated heavy byproduct stream is recycled.

Particular chlorinated propanes formed in the initial reaction may be 1,1,1,3-tetrachloropropane and/or 1,1,1,3,3-pentachloropropane. Chlorinated propenes formed from the dehydrohlorination reactions depends on which chlorinated propane is being converted. Generally, a chloride is removed and a double bond is added during the reaction. For instance, the 1,1,1,3-tetrachloropropane may convert to one or more of 1,1,3-trichloropropene or 3,3,3-trichloropropene, and the 1,1,1,3,3-pentachloropropane to one or more of 1,1,3,3-tetrachloropropene and 1,3,3,3-tetrachloropropene.

(II) Chlorinated Propane Production Reaction

As disclosed herein the process may begin with a chlorinated propane producing reaction, which may be a telomerization reaction. Any method may be employed for producing the desired one or more chlorinated propanes. In order to form the desired chlorinated propane, a reaction mixture may be formed including a chlorinated methane, an alkene or chlorinated alkene, a metal catalyst, and a promoter. These components together react to form a crude chlorinated propane product, which includes the desired chlorinated propane product, as well as other heavy byproduct chlorinated alkanes, the metal catalyst, promoter, and complexes of the catalyst and promoter. In order to induce the reaction, the reaction mixture may be stirred and heated.

In some methods the formation of the chlorinated propane may be considered a telomerization reaction. Telomerization reaction may be considered a form of polymerization and may involve a free radical mechanism. The telomerization involves a reaction of a telogen with a taxogen to produce a telomere. According to the present disclosure, the chlorinated methane may be considered the telogen and the alkene and/or chlorinated alkene the taxogen, and wherein the telomerization produces one or more of the aforementioned chlorinated alkanes having one more carbon than the alkene and/or chlorinated alkene.

(a) Chlorinated Propane

The desired chlorinated propane formed from the reaction may be any chlorinated propane. While the base hydrocarbon has three carbons, any number of chlorines may be attached to the propyl backbone, including one, two, three, four, five, six or more chlorine atoms. A particular number of chlorine atoms may include four or five. The chlorines may be placed on the first, second or third carbon in the propane hydrocarbon chain. There may be one, two or three chlorides on the first carbon, and/or one or two on the second carbon, and/or one, two or three on the third carbon, or mixtures of the aforementioned. In some examples, there may be two or three chlorides on the first carbon, and one or two chlorides on the third carbon.

The at least one chlorinated propane may be selected from one or more of a monochloropropane, dichloropropane, a trichloropropane, a tetrachloropropane, a pentachloropropane, a hexachloropropane, and combinations thereof. Non-limiting examples of trichloropropanes, tetrachloropropanes, pentachloropropanes, and hexachloropropanes include 1,1-dichloropropane, 1,2-dichloropropane, 1,3-dichloropropane, 1,1,1-trichloropropane, 1,1,2-trichloropropane, 1,2,2-trichloropropane, 1,2,3-trichloropropane, 1,1,1,2-tetrachloropropane, 1,1,2,2-tetrachloropropane, 1,1,1,3-tetrachloropropane, 1,1,2,3-tetrachloropropane, 1,1,3,3-tetrachloropropane, 1,1,1,2,3-pentachloropropane, 1,1,2,3,3-pentachloropropane, 1,1,2,2,3-pentachloropropane, 1,1,1,3,3-pentachloropropane, 1,1,1,3,3,3-hexachloropropane, 1,1,2,2,3,3-hexachloropropane, or combinations thereof.

Particular chlorinated propanes include 1,1,1,3-tetrachloropropane (250fb) and/or 1,1,1,3,3-pentachloropropane (240fa).

(b) Chlorinated Methane

The reaction includes a first compound capable of initiating a free radical reaction, including for example compounds capable of decomposition releasing one or two radicals, such as a radical halogen, and in particular chloride. This first compound may include any chlorinated methane, such as a methane with one, two, three, or four chlorides. Examples of chlorinated methane include one or more of methyl chloride (monochloromethane), dichloromethane, chloroform (trichloromethane), or carbon tetrachloride. A particular example includes carbon tetrachloride.

The first compound may include halogens in addition to chloride, such as fluoride, bromide, or iodide. Such compounds include for example dichloromonofluoromethane, trichlorofluoromethane, difluorochloromethane, trifluorochloromethane, bromochloromethane, dibromochloromethane, tribromochloromethane, chloroiodomethane, chlorodiiodomethane, chlorotriiodomethane, bromochlorofluoromethane, bromochlorodifluoromethane, chlorodibromofluoromethane, bromochlorofluoroiodomethane, bromochlorodiiodomethane, and combinations thereof.

The chlorinated methane may be in a liquid phase and may serve as the solvent for the reaction. The metal catalyst, promoter, and any phase transfer catalyst may be a part of the liquid phase, for example dissolved or mixed in the liquid phase as well.

(c) Alkene or Haloalkene

The first compound is reacted with a second compound, the second compound being an alkene (also referred to as olefin) or haloalkene (also referred to as a halogenated alkene). The halogen of the haloalkene may include one or more of chloride, fluoride, iodide, or bromide, or combinations thereof. In particular, the haloalkene is chloroalkene. The haloalkene may include one or more chlorides, and in addition to the one or more chlorides, may include one or more other halogens.

The alkene or haloalkene may have from one to six carbon atoms, for instance one, two, three, four, five, or six carbons, and may be linear, branched or cyclic. Non-limiting examples of alkenes may be ethene, propene, 1-butene, 2-butene, isobutene, 1-pentene, 2-pentene, 3-pentene, 2-methyl-2-butene, 2-methyl-1-butene, and 3-methyl-1-butene. Non-limiting examples of haloalkenes may be chloroethene (also referred to as vinyl chloride), vinyl bromide, vinyl fluoride, allyl chloride, allyl fluoride, 1-chloro-2-butene, 1-fluoro-2 butene, 3-chloro-1-butene, 3-fluoro-1-butene, 3-chloro-1-pentene, 3-fluoro-1-pentene, and combinations thereof. In particular examples, the alkene is ethene and the haloalkene is chloroethene (monochlorethene).

The reaction for the formation of one or more chlorinated propanes includes reacting a chloromethane with ethylene or vinyl chloride in the presence of a catalyst and a promoter. The reaction may optionally include a phase transfer catalyst.

In general, the chlorinated methane may be used in excess. Generally, the molar ratio of the chlorinated methane to the second compound, which may be an alkene and/or haloalkene may range from about 0.1:1 to about 100:1, or from about 0.5:1 to about 75:1, or from about 0.9:1 to about 20:1 or from about 1:1 to about 10:1, or from about 1.2:1 to about 5:1, or combinations of the aforementioned.

The alkene or haloalkene may be in the gas phase and introduced into the reaction in the gas phase. The alkene or haloalkene may be admixed with the liquid phase having the chlorinated methane to carry out the reaction as described further below. Various methods of mixing the gaseous alkene or haloalkene with the chlorinated liquid reaction mixture may be employed, including jet mixing, eduction, packed or trayed absorption columns or spray absorbers.

(d) Catalyst

The chlorinated propane producing reaction may be carried out in the presence of a metal catalyst. The term metal catalyst herein refers to a metal element, metal salt, metal alloy, or other forms or compounds containing the metal or combinations of these. The metal may be a transition metal or transition metal salt. As used herein, the term "transition metal catalyst" refers to a transition metal element, a transition metal salt, a transition metal containing alloy, or combinations thereof. Non-limiting examples of transition metals in the at least one catalyst may include iron and copper. A particular example of a useful catalyst includes iron chloride ($FeCl_2$ or $FeCl_3$). As appreciated by the skilled artisan, the oxidation state of suitable metals may vary, and may be, for example, (0), (I), (II), and (III). Non-limiting examples of suitable transition metals may be copper (0), copper (I), copper (II), iron (0), iron (II), and iron (III).

In an embodiment, the at least one catalyst may be in the form of a salt. These may include a salt with an organic compound as a counter-ion to the metal. Non-limiting examples of suitable metal salts may include acetates, acetyacetonates, alkoxides, butyrates, carbonyls, dioxides, halides, hexonates, hydrides, mesylates, octanates, nitrates, nitrosyl halides, nitrosyl nitrates, sulfates, sulfides, sulfonates, phosphates, and combinations thereof. Non-limiting examples of suitable metal salts may include copper chloride, copper bromide, copper iodide, iron chloride, iron bromide, iron iodide, iron bromide, copper oxide, and iron oxide.

Non-limiting examples of alloys may be gliding metal, bronze, magnesium bronze, tin bronze, aluminum bronze, phosphor bronze, red brass, brass, cast iron, pig iron, steel, tool steel, and wootz steel.

The molar ratio of the soluble metal salt or metal complex catalyst to the chlorinated methane may range from about 0 to about 0.1:1, or from about 0.0001:1 to about 0.05:1, from about 0.0025:1 to about 0.01:1, or from about 0.005:1 to about 0.008:1, or from about 0.001:1 to about 0.007:1, or combinations of the aforementioned.

In some embodiments, at least one metal component of the catalyst is a solid, and the ratio of the surface area of the solid metal catalyst to the halogenated methane comprising at least one chlorine atom may be at least 0.1 $cm^2/(g/hr)$. In another embodiment, the ratio of the surface area of the catalyst to the halogenated methane comprising at least one chlorine atom is at least 1.0 $cm^2/(g/hr)$.

The solid metal catalyst may be in the form of a foil, a sheet, a screen, a wool, a wire, a ball, a plate, a pipe, a rod, a bar or a powder. In various embodiments, the at least one catalyst may be mobilized on the surface of a support. Non-limiting examples of suitable supports may be alumina, silica, silica gel, diatomaceous earth, carbon and clay.

The solid metal catalyst, if present, may be part of a fixed catalyst bed. The solid metal catalyst may be part of a cartridge. Additionally, the solid metal catalyst may be part of a structured or un-structured packing where the metal is a part of the packing or un-structured packing. Using a fixed bed, a cartridge, structured packing, or unstructured packing, the catalyst may be contained and easily replaced.

(e) Promoter

In various embodiments, a promoter may be employed in the first chlorinated propane production reaction. The promoter may be a phosphorus containing compound. The phosphorus containing compound, as the skilled artisan appreciates, may form a complex with the metal catalyst, and in particular a transition metal catalyst, forming a transition metal phosphorus containing compound complex which is soluble within the reaction media. Non-limiting examples of phosphorus containing compound may include alkylphosphates or alkylphosphites such as trialkylphosphates, trialkylphosphites, or combinations thereof. Suitable non-limiting examples of trialkylphosphates and trialkylphosphite may include triethylphosphate, tripropylphosphate, triisopropylphosphate, tributylphosphate ("TBP"), trimethylphosphite, triethylphosphite, tripropylphosphite, triisopropylphosphite, tributylphosphite, and tri-tert-butylphosphite. The phosphorus containing compound is a trialkylphosphate, namely tributylphosphate.

(f) Reaction Conditions

The chlorinated propane producing reaction may be run in a batch mode or a continuous mode, with continuous mode. In a continuous mode, a stirred tank reactor may be used, or a series of stirred tank reactor to approach the performance of an ideal plug flow reactors may be utilized to improve the overall efficiency of the process. The process in continuous modes may be stirred in various methods to improve the mixing of the gas-liquid-solid system as appreciated by the skilled artisan.

In general, the process for the preparation of halogenated alkanes will be conducted to maintain the temperature from about 80° C. to about 140° C. using an internal or external heat exchanger. The temperature of the reactor may be partially maintained by boiling off or vaporizing a portion of the reactants and products. The temperature of the reaction may be maintained from about 80° C. to about 140° C., from 85° C. to about 130° C., from 90° C. to about 120° C., or from about 95° C. to about 115° C.

The process may be conducted at a pressure of about atmospheric pressure (14.7 psi) to about 200 psi so the amount of the gases and liquid are in suitable quantities so the reaction may proceed and maintain the kinetics of the process. The preferred pressure of the process may depend on the reactants being fed. In embodiments wherein the taxogen is ethylene, the pressure of the process may be from atmospheric pressure (14.7 psi) to about 200 psi, from about 50 psi to about 150 psi, or from about 90 psi to about 130 psi. In embodiments wherein the taxogen is chloroethylene (vinyl chloride), the pressure of the process may be from about atmospheric to about 100 psi, from atmospheric to about 70 psi, or from atmospheric to about 50 psi.

The reaction is allowed to proceed for a sufficient period of time until the reaction is complete, as determined by any method known to one skilled in the art, such as chromatography (e.g., GC-gas chromatography). The duration of the reaction, or the residence time in a continuous reactor, may be less than 10 hours, or alternatively, less than 7 hours, or alternatively, less than 5 hours, or alternatively less than 3 hours, with a lower limit of sufficient time to permit the reaction to go completion or near completion, such as 5 minutes, or 30 minutes, or 1 hour, and may range from about 5 minutes to about 16 hours, or 5 minutes to about 12 hours, from about 10 minutes to about 10 hours, from about 30 minutes to about 7 hours, or from about 1 hour to about 5 hours.

As mentioned the chlorinated methane may be in the liquid phase along with the chlorinated alkane product, the metal catalyst, promoter, and any phase transfer catalyst. The alkene and/or chlorinated alkene may be the gas phase and/or introduced into the reaction in the gas phase. The gas phase and liquid phase may be contacted or admixed to induce the reaction, with greater admixture facilitating a more effective reaction. For instance, the reaction mixture may be mixed or stirred to increased gas absorption into the liquid phase. Non-limiting methods to adequately stir the liquid phase contents of the reactor may be jet stirring, eductors, impellers, baffles in the reactor, nozzles, spray nozzles, or combinations thereof. Jet stirring may employ an eductor and/or a nozzle. In some examples, the liquid phase is pumped through a spray nozzle into the gas phase resulting in absorption of the gas into the liquid spray. Alternatively or additionally, a nozzle may be positioned at the surface of the liquid phase or directed through the gas phase into the liquid phase, thereby providing increased turbulence of the reaction mixture but also providing increased absorption of the gas phase into the liquid phase.

The reaction mixture of the first and second compounds thereof are essentially dry, i.e., it has a water content of the below 1000 ppm. Lower water concentrations may desirable, but not required.

(III) Separation of the Crude Chlorinated Propane Stream

After production of the crude chlorinated propane, the exit stream may be subject to separations in a separations unit. The separations process step separates the desired one or more chlorinated propanes from one or more heavy byproducts, and other reaction components. In the separations process, the desired chlorinated propanes and lower boiling compounds may be separated to a first stream, and the heavy byproducts and high boiling reaction components such as catalysts and promoters may be separated to a second stream. The first stream may be a light fraction, or a top stream, and the second stream may be a heavy fraction, or a bottoms stream. Accordingly, these may be separated according to boiling point or on the basis of other properties. Alternatively, the components lower boiling than the desired chlorinated propanes may be separated from the crude chlorinated product first, and then the desired chlorinated propanes may be separated in a light fraction from the heavy fraction.

While some separations process steps may cause most, and very close to all, the chlorinated propanes in the crude product stream to separate into the top fraction, in practice, there is desired chlorinated propanes which end up separated into the heavy fraction stream. This may be due to natural inefficiencies, complexity of chemistry and the separation process, cost, as well as the tuning of the separations unit. Whatever the cause, not all of the desired chlorinated propanes are separated to the top stream, and at least a portion is separated to the bottoms stream. As disclosed herein, these chlorinated propanes may be converted to chlorinated propenes by treatment with an aqueous base. Therefore, the majority of the desired chlorinated propane from the crude chlorinated propane product are separated into the light fraction and converted to chlorinated propenes via a reaction with a Lewis acid catalyst, and the remaining chlorinated propanes in the heavy fraction are converted to chlorinated propenes via aqueous base.

Accordingly, the light fraction may have at least half of the chlorinated propane from the crude product stream, or alternatively, at least greater than half of the chlorinated propane from the crude product stream.

In some embodiments, the majority of the chlorinated propane from the crude product stream is separated to the light fraction. For instance, the conditions of the separator may be set so that most of the chlorinated propane is separated to the light fraction. Accordingly, the amount of chlorinated propane from the crude product stream separated to the light fraction may range from about 50% to about 99%. Such ranges may include at least 70%, alternatively at least 90%, alternatively at least 95%, alternatively at least 99%, however, less than 100% of chlorinated propanes in the crude product mixture, with the remaining chlorinated propanes separating to the heavy fraction.

As the heavy fraction is to be treated and the chlorinated propanes converted to chlorinated propenes rather than disposed of, the separator can be adjusted to relax conditions so as to permit greater amounts of chlorinated propanes to be separated to the heavy fraction. This may save costs as the separator need not be required to recover as much chlorinated propane in the light fraction. Accordingly, a lesser percent of the chlorinated propane from the crude stream may be separated to the light fraction such as about 50% to about 90%, or 50% to 70%, and therefore the light fraction may have chlorinated propane from the crude product stream of at least 50%, alternatively greater than 50%, alternatively at least 55%, alternatively at least 60%, alternatively at least 70%, alternatively at least 75%, alternatively at least 80%, alternatively at least 85%.

The light fraction itself may be made up mostly of the chlorinated propane product, such as greater than 50 wt %, alternatively at least 60 wt %, alternatively at least 75 wt %, alternatively at least 90 wt %, alternatively at least 95 wt %, alternatively at least 99 wt %.

Accordingly, the light fraction may have residual of components other than the desired chlorinated propanes, which may be for example residual chlorinated methane from the first reaction, alkene and/or chlorinated alkene from the first reaction, heavy byproducts, and other chlorinated alkanes or alkenes other than the desired chlorinated propane. The residual chlorinated methane, alkene and/or chlorinated alkene from the first reaction may make up less than 50 wt %, alternatively, less than 30 wt %, alternatively, less than 10 wt %, alternatively less than 5 wt % of the light fraction. The heavy-byproducts may make up less than 5 wt %, alternatively, less than 3 wt %, alternatively, less than 2 wt %, alternatively less than 1 wt %, alternatively less than 0.5 wt % of the light fraction. These components other than the desired chlorinated propanes can be further removed and the chlorinated propane light fraction further purified to increase the concentration of the desired chlorinated propanes. Any components removed from the light fraction may be recycled to the first reaction, or disposed.

The separations unit may be a flash column or a multistage distillation column. Generally it is preferred to operate the separations unit at the lowest temperature possible that will effect vaporization of the light fraction, and for this reason the unit is preferably run under vacuum. Lower temperature results in less catalyst and/or promoter degradation. The unit may operate at a temperature from about 70° C. to about 130° C., or from about 90° C. to about 120° C., or from about 95° C. to about 115° C. The pressure in the unit may be from 5 torr to about 50 psi, from about 30 torr to atmospheric pressure, or from about 50 torr to about 200 torr. Operation at higher vacuum increases the capital and operating cost. In order to maintain low temperature at moderate vacuum, it is therefore desirable to leave part of the chlorinated propane product in the bottom heavy fraction, up to about 30% to about 70% of the bottom fraction by weight.

The heavy byproducts which are separated into the heavy fraction are other chlorinated alkanes or chlorinated alkenes in the crude product stream which are not desired or will not be converted to the desired chlorinated propenes and may be otherwise disposed of. Heavy byproducts are those having a higher boiling point than the desired chlorinated propanes. The one or more chlorinated propanes which are separated into the light fraction are those previously mentioned, and in particular, include 1,1,1,3-tetrachloropropane (250FB) and/or 1,1,1,3,3-pentachloropropane (240fa). Accordingly, the heavy byproducts are those that have a higher boiling point than the desired chlorinated propanes which are in the crude chlorinated propane stream. Therefore, when 1,1,1,3-tetrachloropropane is the chlorinated propane, the heavy byproducts are those with a heavier boiling point, and include those with a greater number of chlorines and/or greater number of carbons. These include for instance tetrachlorpentanes (1,1,1,5- and/or 1,3,3,5-) and/or smaller amounts of pentachloropropanes. When 1,1,1,3,3-pentachloropropane (240fa) is the chlorinated propane, the heavy byproducts may include for instance hexachloropentanes and smaller amounts of hexachloropropanes.

The heavy fraction itself may include the desired chlorinated propane, such as at least 30 to 70 wt %, alternatively from 35 to 50 wt %, or alternatively at least 25 wt %, alternatively at least 30 wt %, alternatively at least 35 wt %, alternatively at least 40 wt %, alternatively at least 50 wt %.

The other reaction components in the heavy fraction may include reactants, products or reagents from the first chlorinated propane production reaction including the metal catalyst, promoter, complexes of the metal catalyst and promoter, and phase transfer catalyst if present. The heavy fraction also includes the remaining chloropropanes which did not separate to the light fraction.

The separation may be carried out by a separation unit. This separation unit may separate the components based on boiling point. The separation unit may include a distillation column or flash unit and may be conducted under vacuum or one atmosphere. Various distillation columns may be used in this capacity. The distillation column may be a single or multistage distillation column, and/or a dividing wall column. The distillation columns may include a side draw and/or a bottom stage, and combinations thereof. The separation unit may be made up of one or two, or more sub-separation units. The separation unit may include a reboiler. In some embodiments, a side draw column or a distillation column which provides an outlet stream from an intermediate stage or a dividing wall column (dividing wall column (DWC) is a single shell, fully thermally coupled distillation column capable of separating mixtures of three or more components into high purity products) may be used as a separator. A portion of various product streams produced by the process may be recycled back into the reactor to provide increased kinetics, increased efficiencies, reduced overall cost of the process, increased selectivity of the desired halogenated alkane, and increased yield of the desired halogenated alkane.

(IV) Catalytic Dehydrochlorination of Light Fraction Stream to Chlorinated Propenes The top stream from the separation unit, in particular the light fraction or further purified light fraction, may be subject to a dehydrochlorination reaction using a catalyst. The catalyst may be a Lewis acid catalyst and the reaction may be carried out in a reactor vessel. The Lewis acid catalyst may be dissolved in a solvent prior to being added to the reactor. The Lewis acid catalyst may be a homogeneous or a heterogeneous catalyst. In various embodiments, the Lewis acid catalyst comprises gallium, iron, aluminum, or combinations thereof. Non-limiting examples of these Lewis acid catalysts may be gallium metal, a gallium salt, a gallium alloy, iron metal, an iron salt, an iron alloy, aluminum, aluminum salt, aluminum alloy or combinations thereof. Iron may be in any of its oxidation states including Fe(I), Fe(II), and Fe(III), and gallium may have any of its oxidation states including Ga(I), Ga(II), and Ga(III).

For salts of gallium, iron, and/or aluminum, suitable anions include organic or halide anions, including acetates, acetyacetonates, alkoxides, butyrates, carbonyls, dioxides, hexonates, hydrides, mesylates, octanoates, nitrates, nitrosyl halides, nitrosyl nitrates, sulfates, sulfides, sulfonates, phosphates, chloride, fluoride, iodide, bromide, and combinations thereof. A particular example ion is chloride.

Particular exemplary catalysts include iron chloride ($FeCl_3$), gallium chloride ($GaCl_3$), and/or aluminum chloride ($AlCl_3$). Non-limiting examples of the forms or configuration of Lewis acid catalyst may be a dissolved species in a liquid phase, a species deposited on a solid support, a packing, an unstructured packing, a foil, a sheet, a screen, a wool, a wire, a ball, a plate, a pipe, a rod, a bar, a salt, or a powder.

The weight % (wt %) of the Lewis acid catalyst in the reaction mixture may range from about 0.0001 wt % to about 2.0 wt %. The reaction may be anhydrous, with less than 100 ppm water. The reaction temperature may be 50 to 200° C., or 100 to 175° C., or 120 to 165° C. The reaction pressure may be 20 torr to 200 psig, 30 torr to atmospheric pressure, or 50 torr to 200 torr. The reaction may be operated as a reactive distillation, wherein products such as HCl and/or the chlorinated propene are removed from the reactor as an overhead stream as the reaction progresses. The extent of removal will be dictated by the operating temperature and pressure.

The conversion of the chlorinated propanes to chlorinated propenes may be at least 85% or at least 90% or at least 95% or at least 98%. The selectivity to chloropropenes may be at least 85% or at least 90% or at least 95% or at least 98%.

The same type of reactor and mixing methods employed in the first chlorinated propane producing reaction may be applied in the catalytic dehydrochlorination reaction. As such, the reaction may be carried out in any reactor including a reactor made of carbon steel or an inert material, such as hastelloy, tantalum, or a glass lined reactor. Jet stirring, eductors, nozzles, impellers and/or baffles may be employed for stirring or mixing the contents to induce an efficient and full reaction. The reactor may be a reactive distillation, in which the chlorinated propene product, HCl byproduct, or both are continuously vaporized and distilled overhead from the liquid reaction mixture.

The chlorinated propene product formed depends on which chlorinated propane was formed in the first chlorinated propane producing reaction.

(V). Caustic Dehydrochlorination and Precipitation Reaction of the Bottom Stream

(a) Treatment of Heavy Fraction with Caustic

The bottoms stream from the separation unit, in particular the heavy fraction, may be treated with caustic, such as an aqueous base for a parallel precipitation reaction and dehydrochlorination reaction. The heavy fraction may be diluted with a chlorinated methane or other suitable solvent, particularly carbon tetrachloride, prior treatment with caustic. The caustic treatment results in (1) the metal from the metal catalyst being precipitated as metal hydroxide and (2) the chlorinated propane in the heavy fraction being converted to one or more chlorinated propenes. The addition of the aqueous base to the heavy fraction forms an aqueous phase and an organic phase. The metal from the metal catalyst is precipitated into the aqueous phase, whereas the chlorinated propenes are formed in the organic phase. The aqueous phase and the organic phase may thereafter be separated so as to reuse the catalyst or promoter and produce chlorinated propenes in a separate stream.

The treatment of the heavy fraction stream may be with an aqueous base. The base may be an inorganic base such as an alkali or alkali earth metal hydroxide. The inorganic base may be an alkali or alkali earth metal hydroxide. Non-limiting examples of these alkali metal or alkali earth metal bases may include LiOH, NaOH, KOH, $Ba(OH)_2$, $Ca(OH)_2$, $Na_2CO_3$, $K_2CO_3$, $NaHCO_3$, $KHCO_3$, or combinations thereof. In particular, the alkali or alkali earth metal base may include NaOH, KOH, or combinations thereof, and in particular NaOH. During the dehydrochlorination reaction the base may react with one or more of the chlorines or other halogens of the compounds in the heavy fraction and may thereby form an alkali or alkali earth metal chloride salt. A particular salt that may be formed as a result of the dehydrochlorination reaction described herein is sodium chloride.

The concentration of the inorganic base in water may range from 5 wt % to about 50 wt %. In various embodiments, the concentration of the dehydrochlorination reagent may range from 5 wt % to about 50 wt %, from 7 wt % to about 40 wt %, from 9 wt % to about 30 wt %, or from 10 wt % to about 20 wt %. In a particular embodiment, the concentration of the inorganic base may range from 5 wt % to about 12 wt %.

In general, the mole ratio of the base to the chlorinated propane may range from to about 2.0:1.0. In various embodiments, the mole ratio of the base to the chlorinated alkane may range from 0.1:1.0 to about 2.0:1.0, or from 1.0:1.0 to about 1.75:1.0, or from 1.05:1.0 to about 1.3:1.0. When other components in the feed to the dehydrochlorination reactor are dehydrochlorinated, such as heavy byproducts from the first reaction, these ranges may also apply to the mole ratio of the base to the total of the components that can be dehydrochlorinated.

The conversion of the chlorinated propanes to chlorinated propenes may be at least 85% or at least 90% or at least 95% or at least 98%. The selectivity to chloropropenes may be at least 85% or at least 90% or at least 95% or at least 98%.

The temperature of the process may vary depending on concentration of the compounds involved, the type of chosen base, and the concentration of the base. Generally, the temperature of the process may be generally from about 20° C. to about 120° C., alternatively from about 45° C. to about 95° C., or from about 55° C. to about 85° C.

Generally, the pressure may range from about 0 psig to about 1000 psig, from about 0 psig to about 500 psig, or from about 0 psig to about 200 psig, or from about 0 psig to about 40 psig. The process may be conducted under an inert atmosphere such as nitrogen, argon, or helium.

The precipitation and dehydrochlorination process may be run in a batch mode or a continuous mode. The process may be stirred by the methods disclosed herein to improve the mixing of the biphasic system. The same type of reactor and mixing methods employed in the first chlorinated propane producing reaction may be applied in the catalytic dehydrochlorination reaction. As such, the reaction may be carried out in any reactor including a reactor made of carbon steel or an inert material, such as hastelloy, tantalum, or a glass lined reactor. Jet stirring, eductor, nozzles, impellers and/or baffles may be employed for stirring or mixing the contents to induce an efficient and full reaction. Jet mixing may include feeding fresh liquid feed, product effluent stream, a recycle stream or combinations thereof to at least one nozzle. In this jet stirred reactor system, the liquid materials comprising internal recycle, fresh feed or both are introduced vertically, tangentially or radially into the reactor by means of an external pump.

The reaction may be allowed to proceed for a sufficient period of time until the reaction is complete.

In some instances the caustic dehydrochlorination may utilize a phase transfer catalyst. Non-limiting examples of phase transfer catalysts may be quaternary ammonium salts, phosphonium salts, and pyridinium salts. In some embodiments, the phase transfer catalyst may be a quaternary ammonium salt. Non-limiting examples of suitable salts are chlorides, bromides, iodides, or acetates. Non-limiting examples of quaternary ammonium salts include trioctylmethylammonium chloride (Aliquat® 336), trioctylmethylammonium bromide, dioctyldimethylammonium chloride, dioctyldimethylammonium bromide, Arquad 2HT-75, benzyldimethyldecylammonium chloride, benzyldimethyldecylammonium bromide, benzyldimethyldecylammonium iodide, benzyldimethyltetradecylammonium chloride, dimethyldioctadecylammonium chloride, dodecyltrimethylammonium chloride, tetrabutylammonium chloride, tetrabutylammonium bromide, tetrabutylammonium iodide, tetrabutylammonium acetate, tetrahexylammonium chloride, tetraoctylammonium chloride, tridodecylmethylammonium chloride, tetraethylammonium chloride, tetraethylammonium bromide, tetraethylammonium iodide, or combinations thereof. In some embodiments, more than one phase transfer catalyst is used. In a preferred embodiment, the phase transfer catalyst is trioctylmethylammonium chloride (Aliquat® 336).

A chlorinated methane, in particular carbon tetrachloriede, may be added to the heavy fraction prior to the caustic dehydrochlorination. This may assist with phase separation as well as stripping out the chlorinated propene product from the organic phase.

The amount of the phase transfer catalyst may range from about 0.1 wt % to about 5.0 wt % based on the total weight of the components, alternatively from about 0.3 wt % to about 1 wt %, or from about 0.4 wt % to about 0.7 wt %. The amount of phase transfer catalyst addition to achieve these concentrations will depend on the amount already in the heavy fraction from the first reaction, if present.

(b) Reaction Products

The precipitation reaction and the dehydrochlorination reaction from contact with the aqueous base results in the formation of a crude chlorinated propene product, which makes up the organic phase of the reaction product. The crude chlorinated propene product includes chlorinated propenes as well as other byproducts and reaction components. The dehydrochlorination reaction products depend on which chlorinated alkanes were provided to the reaction. Generally, the dehydrochlorination reaction results in the loss of a chloride and the formation of a double bond in the compound being dehydrochorinated. In some embodiments, the dehydrochlorination of tetrachloropropanes results in trichloropropenes, and the dehydrochlorination of pentachloropropanes results in tetrachloropropenes, and the dehydrochlorination of hexchloropropanes results in pentachloropropenes.

Exemplary chlorinated propene products include 1,1,3-trichloropropene, 3,3,3-trichloropropene, 1,2,3-trichloropropene, 1,1,3,3-tetrachloropropene, 1,3,3,3-tetrachloropropene, and mixtures thereof. In particular, 1,1,1,3-tetrachloropropane (250fb) dehydrochlorinates to one or more of 1,1,3-trichloropropene or 3,3,3-trichloropropene. 1,1,1,3,3-pentachloropropane (240fa) dehydrochlorinates to one or more of 1,1,3,3-tetrachloropropene, 1,3,3,3-tetrachloropropene.

In addition to the desired chlorinated propenes, the crude chlorinated propene product includes other byproducts including other chlorinated alkanes and alkenes. This may include heavier components which have a higher boiling point than the desired chlorinated propenes. Furthermore, there may be residual components from the first chlorinated alkane production reaction, such as the promoter, and/or phase transfer catalyst.

In addition to dehydrochlorination of chlorinated propanes, the treatment with the aqueous base also produces precipitation reaction products. In particular, the metal from the metal catalyst employed in the first chlorinated propane producing reaction precipitates into the aqueous phase. The metal from the catalyst reacts with the base to form a metal hydroxide. Accordingly, the products of the precipitation include metal hydroxides from the metal catalyst, and so the product formed depends on the metal employed in the metal catalyst. Non-limiting examples of the precipitate products include iron hydroxide and/or copper hydroxide, or other alloys or metals that were used as the metal catalyst in the first chlorinated propane producing reaction. The reaction with the base also forms a salt byproduct, which may be for example alkali metal or alkali earth metal halide, such as sodium chloride.

(VI) Separation of the Caustic Reaction Products

The treatment with the aqueous base forms a stream having an aqueous phase and an organic phase. The aqueous phase comprises the metal precipitated from the metal chloride and the organic phase, or crude chlorinated propene, includes chlorinated propanes, chlorinated propenes and heavy byproducts and promoter from the first reaction and phase transfer catalyst, if used. The aqueous phase and the organic phase may be separated from one another. The aqueous phase and organic phase can then be treated or disposed of separately. The aqueous phase may be treated to remove the metal hydroxide from the aqueous phase. For instance, the solid metal hydroxide may be removed by conventional solid techniques such as settling, filtration, or centrifuging. This removal of the metal hydroxide can be conducted in the reactor, after removal from the reactor, and/or after separation of the aqueous phase from the organic phase.

The metal hydroxide precipitate may be used for producing catalyst or may be otherwise disposed of. Alternatively, the metal hydroxide may be left in the aqueous phase and the mixture disposed of by sending to a wastewater treatment facility.

(VII) Separation of Crude Chlorinated Propene Reaction Product

The removal of the metal from the organic phase facilitates further treatment, recycle and/or incineration of components of the crude chlorinated propene reaction product. This exit stream from the caustic reaction may be fed to a second separation unit. The second separation unit separates the crude chlorinated propene stream into a light fraction having purified chlorinated propenes and a heavy fraction. The bottom heavy fraction comprises heavy byproducts including chlorinated alkanes and alkenes. These heavy byproducts have boiling points greater than the desired chlorinated propenes in the light fraction. The heavy fraction also includes reaction components from the first chlorinated alkane producing reaction such as the promoter and any phase transfer catalyst that was fed to the first reaction or the reaction with caustic. The light fraction has a higher concentration of the desired chlorinated propenes than the crude chlorinated propene reaction product, and may include at least 95% chlorinated propenes, alternatively at least 96% chlorinated propenes, alternatively at least 97% chlorinated propenes, alternatively at least 98% chlorinated propenes, alternatively at least 99% chlorinated propenes, alternatively at least 99.9% chlorinated propenes, alternatively at least 99.99% chlorinated propenes.

The heavy fraction may be disposed of, such as provided to an incinerator, or may be recycled to the first chlorinated alkane producing reaction and/or to the first crude chlorinated alkane separator. The light fraction may include water that was dissolved in the organic phase from the caustic dehydrochlorination reaction. The light fraction may be dried to remove water. The light fraction may be provided to the or it may be combined with the chloropropene reaction product from the catalytic dehydrochlorination. If provided to the first crude chlorinated alkane separator, the chlorinated propenes therein will be separated into the light fraction from that separator, along with the chlorinated propanes to be sent to the catalytic dehydrochlorination reaction.

This separation may carried out employing a similar separation unit as earlier described herein. This separation unit may separate the components based on boiling point. In particular, the separation unit may include a distillation column or flash unit and may be conducted under vacuum or atmosphere. Exemplary distillation columns include single or multistage distillation column, and/or a dividing wall column. The separation unit may include a distillation column or flash unit and may be conducted under vacuum or atmospheric pressure.

(VIII) Separation of Crude Chlorinated Propene Product from the Catalytic Dehydrochlorination Reaction Returning again to the catalytic dehydrochlorination, as mentioned this reaction produces a chlorinated propene product. This chlorinated propene product may be provided to a separation unit. Prior to being fed to the separation unit, this chlorinated propene product may be combined with the light fraction which is separated from the chlorinated propene obtained from the caustic dehydrochlorination reaction.

This separator further purifies the chlorinated propenes, producing a light fraction having the purified chlorinated propenes and a heavy fraction including heavy byproducts, such heavy byproducts having a higher boiling point than the chlorinated propenes in the light fraction.

Exemplary Processes

FIG. 1 illustrates an exemplary process 100 for producing additional chloropropenes by treating a byproduct stream. As shown, an initial feed 105 comprising a chlorinated methane, in this case carbon tetrachloride ("Tet"), alkene or haloalkane, in this case ethene (an olefin), and a promoter, in this case TBP, along with a metal catalyst, in this case iron metal and/or iron chloride ($FeCl_3$ and/or $FeCl_2$) is fed to a reactor 110. Reactor 110 may also contain iron metal. The ethene is introduced in the gas phase, and the ethene, TBP, and Tet are in a liquid phase. The gas and liquid may be admixed in the reactor 110 employing jet stirring. The components are reacted in the reactor 110 in a first chlorinated alkane producing reaction. As a result of the reaction, a crude chlorinated propane product 115 is formed having one or more desired chlorinated propanes. These desired chlorinated propanes may be for instance 1,1,1,3-tetrachloropropane (250fb) or, if vinyl chloride is fed to reactor 110 instead of ethylene, 1,1,1,3,3-pentachloropropane (240fa). Both 1,1,1,3-tetrachloropropane and 1,1,1,3,3-pentachloropropane may be produced together, or one or the other may be made. The crude chlorinated propane product 115 comprises other reaction components such as TBP, Tet, iron chloride, complexes of iron chloride and TBP and heavy byproducts.

These heavy byproducts in the crude chlorinated propane product 115 include chlorinated alkanes and/or alkenes which have one or more carbons or one or more chlorides than the desired 1,1,1,3-tetrachloropropane and 1,1,1,3,3-pentachloropropane. These heavy byproducts may have a higher boiling point than the one or more desired chlorinated propanes, and may include tetrachloropentanes such as 1,1,1,5-pentachloropropane and/or 1,3,3,5-pentachloropropane, pentachloropropanes, hexachloropentanes, hexachloropentanes or combinations thereof.

The crude chlorinated propane product 115 is then provided to a separation unit 120. The separation unit 120 may be a vacuum distillation column. The crude chlorinated propane product 115 is separated into a light fraction 125 and a heavy fraction 130. At least half the chlorinated propanes from the crude chlorinated propane product 115 are separated into the light fraction 125. The light fraction 125 is a purified stream comprising the desired chlorinated propanes in higher concentration. The light fraction 125 may be further purified to remove any residual reaction components or heavy byproducts (not shown), as the concentration of chlorinated propane in the light fraction 125 may be as low as about 50%, depending on the conversion in the first reaction. The light fraction 125 or further purified light fraction is fed to catalytic dehydrochlorination reactor 130, which has a Lewis acid dehydrochlorination catalyst. The light fraction 125 is then subject to a dehydrochlorination reaction where the chlorinated propane is converted to a crude chlorinated propene stream 195. The crude chlorinated propene stream 195 comprises the desired chlorinated propenes such as 1,1,3-trichloropropene, 3,3,3-trichloropropene, 1,1,3,3-tetrachloropropene, 1,3,3,3-tetrachloropropene, and mixtures thereof. The crude chlorinated propene stream 195 also includes heavy byproducts, having a higher boiling point than the desired chlorinated propenes.

The heavy fraction 135 includes the heavy byproducts from the crude chlorinated propane product 115. These include chlorinated alkanes and alkenes with higher boiling point than the desired chlorinated propanes. Additionally, the heavy fraction 135 includes also components leftover from the reaction in reactor 110, including TBP, iron chloride, and complexes of TBP and iron chloride. The heavy fraction 135 also includes any of the chlorinated propanes remaining which were not separated to the light fraction 125, which may be from 30-70% by weight of the mixture. The requirements of the separation unit 120 may be relaxed to allow greater amounts of chlorinated propane to pass to the heavy fraction 135, as the stream will be treated to produce chlorinated propenes rather than simply disposed of. A portion of the heavy fraction 135 may be recycled in recycle stream 150 back to the reactor 110.

The heavy fraction 135 is provided to a caustic reactor 145. An aqueous base feed 150, in this case NaOH, is fed to the caustic reactor 145. Although not shown, a phase transfer catalyst may also be employed. In this reactor, a precipitation reaction occurs where the iron from the iron chloride precipitates as iron hydroxide in an aqueous phase. An additional byproduct NaCl is also produced as result a dehydrochlorination reaction. The iron hydroxide can be removed via exit stream 155 by settling, filtration or centrifuging. The removal of the iron from heavy fraction 135 improves the catalytic activity of the organic stream if portions of it are recycled to reactor 110 and also facilitates its disposal.

A crude chlorinated propene stream 160 exits the caustic reactor 145. This stream includes the chlorinated propenes produced by the reaction in the caustic reactor 145, as well as heavy byproducts. The stream also includes TBP and any phase transfer catalyst, if any was provided to reactor 110 or caustic reactor 145. The exit stream 160 is fed to a separation unit 165, which may be a distillation column. The chlorinated propenes are separated into the light fraction 170, which may be recycled to the separation unit 120 and/or provided to the crude chlorinated propene stream 195 which exited the catalytic reactor 130. This crude chlorinated propene stream 195 may be provided to a separation unit 196, wherein the desired chlorinated propenes are separated into a light fraction 197, and heavy byproducts, such as those compounds having a higher boiling point than the chlorinated propenes in light fraction 197, are separated to heavy fraction 198.

A heavy fraction 180 is drawn from the separation unit 165. The heavy fraction 180 includes the heavy byproducts, which have a higher boiling point than the chlorinated propenes. All or a portion of this heavy fraction 180 may be recycled to the reactor 110 or the separation unit 120, and all or a portion of this heavy fraction 180 may be disposed of.

Due to treatment of the heavy fraction 120 with the aqueous base in the caustic reactor 150, the iron is removed from this stream, and chlorinated propanes are converted to more useful chlorinated propenes. The removal of the iron allows production of a stream that is more useful for recycling, and the conversion to chlorinated propenes creates useful products rather than the stream otherwise being disposed of and unused.

Accordingly, while the primary conversion of chlorinated propanes to chlorinated propenes may be carried out using a catalytic reaction, the heavy byproduct streams may be caused to have higher value by treating with a caustic so as to remove metal from the catalyst and produce more useful chlorinated propene end products, rather than waste.

Figure 2:
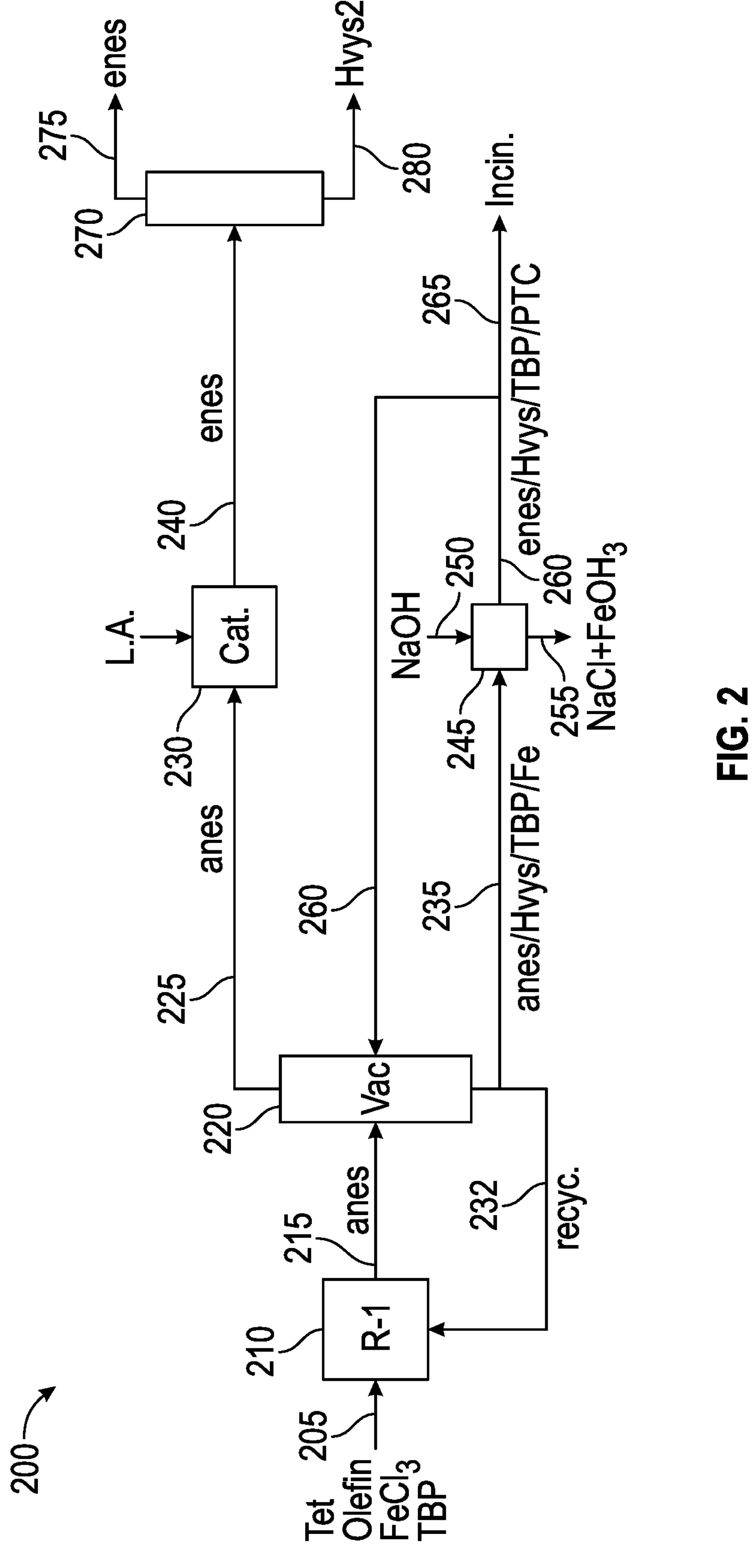
FIG. 2 is a schematic of one exemplary embodiment of a process for the caustic treatment of a heavy byproduct stream.

FIG. 2 illustrates an exemplary process 200 for producing additional chloropropenes by treating a byproduct stream. The process 200 of FIG. 2 is similar to that of FIG. 1 but with fewer recycling steps. As shown an initial feed 205 comprising a chlorinated methane, Tet, alkene or haloalkene, TBP, and iron chloride ($FeCl_3$) is fed to a reactor 210. Reactor 210 may also contain iron metal. The ethene is introduced in the gas phase, and the ethene, TBP, and Tet are in a liquid phase. The gas and liquid may be admixed in the reactor 210 employing jet stirring. The components are reacted in the reactor 210 in a first chlorinated alkane producing reaction.

As a result of the reaction, a crude chlorinated propane product 215 is formed having one or more desired chlorinated alkanes. The crude chlorinated propane product 215 includes other reaction components such as TBP, Tet, iron chloride and complexes of iron chloride and TBP.

The crude chlorinated propane product 215 is then provided to a separation unit 220. The separation unit 220 may be a vacuum flash or distillation column. The crude chlorinated propane product 215 is separated into a light fraction 225 and a heavy fraction 230. At least half the chlorinated propanes from the crude chlorinated propane product 215 are separated into the light fraction 225.

The light fraction 225 is a purified stream comprising the desired chlorinated propanes in higher concentration. The light fraction 225 may be further purified to remove any residual reaction components or heavy byproducts (not shown), as the concentration of chlorinated propane in the light fraction 125 may be as low as about 50%, depending on the conversion in the first reaction. The light fraction 225 or further purified light fraction is fed to catalytic dehydrochlorination reactor 230, which has a dehydrochlorination Lewis acid catalyst. The light fraction 225 is then subject to a dehydrochlorination reaction where the chlorinated propane is converted to a crude chlorinated propene stream 240. The crude chlorinated propene stream 240 also includes heavy byproducts, having a higher boiling point than the desired chlorinated propenes. This crude chlorinated propene stream 240 may be provided to a separation unit 270, wherein the desired chlorinated propenes are separated into a light fraction 275, and heavy byproducts, such as those compounds having a higher boiling point than the chlorinated propenes in light fraction 275, are separated to heavy stream 280.

The heavy fraction 235 includes the heavy byproducts from the crude chlorinated propane product 215. These include chlorinated alkanes with higher boiling point than the desired chlorinated propanes. Additionally, the heavy fraction 235 includes components leftover from the reaction in reactor 210, including TBP, iron chloride, and complexes of TBP and iron chloride. The heavy fraction 235 also includes any of the desired chloropropanes remaining which were not separated to the light fraction 225, which may be from 30-70% of the mixture. A portion of the heavy fraction 235 may be recycled in recycle stream 232 back to the reactor 210.

The heavy fraction 235 is provided to a caustic reactor 245. An aqueous base feed 250, in this case NaOH, is fed to the caustic reactor 245. Although not shown, a phase transfer catalyst may also be employed. In this reactor, a precipitation reaction occurs where the iron from the iron chloride precipitates as iron hydroxide in an aqueous phase. An additional byproduct NaCl is also produced as result of a dehydrochlorination reaction. The iron hydroxide can be removed via exit stream 255 by settling, filtration or centrifuging. The removal of the iron from heavy fraction 235 improves the catalytic activity of the organic stream if portions of it are recycled to reactor 210 and also facilitates its disposal.

A crude chlorinated propene stream 260 exits the caustic reactor 245. This stream includes the chlorinated propenes produced by the reaction in the caustic reactor 245, as well as heavy byproducts. The stream also includes TBP and any phase transfer catalyst, if any was provided in the reactor 210 or caustic reactor 245. A portion of the exit stream 260 may be recycled to the separation unit 220, while the remainder is disposed of via exit line 265. Alternatively (not shown), a portion or all of stream 260 may be combined with stream 240. In this embodiment, the heavy stream 280 from separator 270 will include the combined heavy components from both reactors 245 and 230. Heavy stream 280 could then be partially recycled to separator 220 or reactor 210, the remainder being sent to disposal.

As disclosed herein, the terms chlorinated propane and/or chlorinated propene, and chloropropane and/or chloropropene encompass mono- di-, tri-, penta-forms and encompass all isomers of the compound and all positions of the chloride(s) along the hydrocarbon chain making up the propane or propene base chain. For instance, the term trichloropropenes includes all isomers of trichloropropene, including cis- and trans-, including for instance, 1,1,3-trichloropropene, 2,3,3-trichloropropene, cis-1,2,3-trichloropropene, trans-1,2,3-trichloropropene. Similarly, the term trichloropropanes includes all isomers of trichloropropane, including 1,2,3-trichloropropane. The term tetrachloropropenes includes all isomers of tetrachloropropene including 1,1,2,3-tetrachloropropene and 2,3,3,3-tetrachloropropene. The term tetrachloropropanes includes all isomers of tetrachloropropane including 1,1,2,3-tetrachloropropane and 1,2,2,3-tetrachloropropane. The term pentachloropropanes includes all isomers of pentachloropropane including 1,1,1,2,3-pentachloropropane, 1,1,2,2,3-pentachloropropane, and 1,1,2,3,3-pentachloropropane.

EXAMPLES

To facilitate understanding of the present disclosure, the following examples of certain embodiments are provided, and in no way should the following examples be read to limit the scope of the disclosure.

Example 1: Caustic Treatment of Heavy Fraction from 250fb Production

A telomerization reaction was conducted with carbon tetrachloride and ethylene, iron metal, $FeCl_3$, and tributyl phosphate ("TBP") as a promoter. Crude chlorinated propane product from the telomerization was distilled to remove most of the desired 1,1,1,3-tetrachloropropane (250fb) product and lighter components. The remaining heavy fraction having heavy byproducts weighed 15.65 g. GC analysis of the heavies indicated 2.4 wt % 1-chlorobutane, 54.2 wt % 250fb, 1.6 wt % pentachloropropane isomers, 30.5 wt % tetrachloropentane isomers, 8.6 wt % TBP (organic basis). Iron analysis by extraction into aqueous HCl, reduction of Fe(III) to Fe(II) and analysis of the HCl by the colorimetric, phenanthroline complexation method indicated 1.6 wt % Fe. The TBP content might have been higher due to destruction in the GC inlet.

This crude product stream heavy was mixed with 21.8 g of 19.4% aqueous caustic, 10 g water and 0.1 g Aliquate 336® phase transfer catalyst. After 3.7 hours stirring at 62-68°, the mixture was centrifuged to recover 9.9 g organic phase, 60 g clear aqueous phase (some additional water added) and 3.5 g of precipitated iron hydroxide sludge.

The organic phase was transparent dark brown and free flowing. GC analysis of the organic phase indicated 0.2 wt % chlorobutane, 12.6 wt % 3,3,3-trichloropropene, 18.7 wt % 1,1,3-trichloropropene, 4.9 wt % 250fb, 2.4 wt % pentachloropropane isomers, 32.0 wt % tetrachloropentane isomers and 17.6 wt % TBP. Most of the unspecified components were compounds higher boiling than 250fb (longer retention time on the GC). The increase in TBP was larger than anticipated, probably due to under-reporting TBP content in the starting heavies material, caused by TBP destruction in the GC inlet at high temperature and with high iron.

The treated heavy byproducts were distilled to remove most of the trichloropropene products to produce 6.6 g of a final organic stream containing 4.2 wt % 1,1,3-trichloropropene, 1.3 wt % 250fb, 46.0 wt % tetrachloropentane isomers and 27.2 wt % TBP. All of the unspecified components (21.3 wt %) were higher boiling than 250fb, and about a third of that (7.7 wt %) was higher boiling than the two main tetrachloropentane isomers. The final treated, distilled heavy byproduct material was transparent dark brown and free flowing.

The precipitated iron, which had the form of a sludge, from the caustic treatment was dissolved in HCl, centrifuged and 0.5 g additional organic phase was recovered. The HCl was analyzed and contained 0.3 g Fe. The clear aqueous phase from the caustic treatment was 2.2% NaOH and did not contain detectable organics by GC analysis. The aqueous phase was acidified to precipitate a white solid that was not readily soluble in water or methanol. The solid was washed with methanol, dried and weighed 0.04 g. Energy dispersive x-ray (EDX) analysis of the solid revealed that it contained 59.4 mole % carbon, 2.1 mole % nitrogen, 10.9 mole % phosphorus, 1.4 mole % chlorine and 3.1 mole % iron. The ratio of C/P suggested that the solid was predominantly di- and monobutyl phosphate.

Example 2: Caustic Treatment of Pure 240fa

A telomerization reaction was conducted to produce 26 g of 1,1,1,3,3-pentachloropropane (240fa) (99.2 mole %). This was mixed with 27.4 g of 19.4 wt % aqueous NaOH. The mixture was stirred and heated to an average temperature of 66° C. for 1.5 hours. GC analysis indicated that only 1.3 wt % of the 1,1,1,3,3-pentachloropropane had dehydrochlorinated to tetrachloropropene. To the organic phase was added 0.117 g of Aliquat 336 as a phase transfer catalyst. The mixture was stirred and heated to an average temperature of 65° C. for an additional 3 hours. The organic phase was separated, analyzed by GC and found to contain 42.5 mole % 1,1,3,3,-tetrachloropropene (1230ZA), 18.3 mole % of another tetrachloropropene isomer (presumed to be 1,3,3,3-tetrachloropropene), and 38.1 mole % 240fa. This proves that heavies from 1,1,1,3,3-pentachloropropane production could be treated with caustic to obtain results similar to Example 1 with 1,1,1,3-tetrachloropropane starting material.

The invention claimed is:

1. A process for producing chlorinated propenes comprising contacting, in a first reaction, a chlorinated methane, a metal containing catalyst, a promoter, and an alkene or chlorinated alkene together to form a crude chloropropane product comprising a chloropropane and heavy byproducts with boiling points higher than the chloropropane;

separating, in a crude chloropropane product separation, the crude chloropropane product into a light fraction and a heavy fraction, the light fraction comprising at least half of the chloropropane from the crude chloropropane, and a heavy fraction comprising the remaining chloropropane, the heavy byproducts, the metal containing catalyst, the promoter, and any complexes formed from the promoter and metal containing catalyst; and contacting at least a portion of the heavy fraction with an aqueous base in a second reaction thereby forming an aqueous phase comprising metal precipitated from the metal containing catalyst and an organic phase comprising a first crude chloropropene product comprising chloropropene formed via a dehydrochlorination reaction, separating the aqueous phase from the organic phase; and contacting, in a third and separate dehydrochlorination reaction, the light fraction with a Lewis acid dehydrochlorination catalyst thereby forming a second crude chloropropene product.

2. The process of claim 1, wherein the light fraction is further purified to remove one or more components other than the chloropropane prior to the separate dehydrochlorination reaction.

3. The process of claim 1, wherein a solvent is added to the heavy fraction prior to the second reaction.

4. The process of claim 1, wherein at least a portion of the heavy fraction and/or the organic phase is recycled to the first reaction or to the crude chloropropane product separation.

5. The process of claim 1, further comprising separating the organic phase into a dehydrochlorination light fraction comprising the chloropropene and a dehydrochlorination heavy fraction comprising the promoter, the heavy byproducts and compounds having a higher boiling point than the chloropropene.

6. The process of claim 5, further comprising one or more of recycling at least a portion of the dehydrochlorination heavy fraction to the first reaction, recycling at least a portion of the dehydrochlorination heavy fraction to the crude chloropropane product separation, incinerating at least a portion of the dehydrochlorination heavy fraction, or combinations of these.

7. The process of claim 4, further comprising recycling at least a portion of the dehydrochlorination light fraction to the crude chloropropane product separation, recycling at least a portion of the dehydrochlorination light fraction to the third and separate dehydrochlorination reaction, or a combination of both.

8. The process of claim 1, wherein the precipitated metal is in the form of a metal hydroxide.

9. The process of claim 1, further comprising removing the precipitated metal from the aqueous and organic phases.

10. The process of claim 9, wherein the precipitated metal is washed with a solvent or dissolved in aqueous acid after removal from the aqueous and organic phases.

11. The process of claim 1, wherein the chloropropane is selected from the group of 1,1,1,3-tetrachloropropane, 1,1,1,3,3-pentachloropropane, and mixtures thereof.

12. The process of claim 1, wherein the chloropropene is selected from the group of 1,1,3-trichloropropene, 3,3,3-trichloropropene, 1,2,3-trichloropropene, 1,1,3,3-tetrachloropropene, 1,3,3,3-tetrachloropropene, and mixtures thereof.

13. The process of claim 1, wherein the chlorinated methane is carbon tetrachloride.

14. The process of claim 1, wherein the metal catalyst is a transition metal catalyst.

15. The process of claim 1, wherein the metal catalyst comprises iron metal, $FeCl_3$, or a combination of the two.

16. The process of claim 1, wherein the promoter comprises phosphate, and wherein said phosphate at least partially forms a complex with the metal catalyst.

17. The process of claim 1, wherein the promoter is selected from trialkylphosphate or trialkylphosphite.

18. The process of claim 1, wherein a phase transfer catalyst is present in the second reaction.

19. The process of claim 1, wherein the phase transfer catalyst is selected from a tetraalkylammonium compound, a tetraalkylphosphonium compound, a pyridinium salt, trioctylmethyl ammonium chloride (Aliquat 336), dioctyldimethylamonium chloride, Arquad 2HT-75, benzyldimethyldecylammonium chloride, benzyldimethyltetradecylammonium chloride, dimethyldioctadecylammonium chloride, dodecyltrimethylammonium chloride, methyltrioctylammonium chloride, tetrabutylammonium chloride, tetrahexylammonium chloride, tetraoctylammonium chloride, tridodecylmethylammonium chloride, tetramethylphosphonium chloride, tetraphenylphosphonium bromide, trihexyltetradecylphosphonium chloride, and combinations thereof.

20. The process of claim 1, wherein the dehydrochlorination reaction in the second reaction is conducted at a temperature from 45° C. to 100° C. and a pressure from 0 Pa (0 psig) to 1380 kPa (200 psig).

21. The process of claim 1, wherein the aqueous base is NaOH.

22. The process of claim 1, wherein the NaOH present in the aqueous base contacting the heavy fraction is present from 1 to 20 wt % in the aqueous phase.

23. The process of claim 1, wherein the aqueous base contacting the heavy fraction comprises an alkali metal or alkali earth metal chloride salt selected from a group consisting of lithium chloride, sodium chloride, potassium chloride, barium chloride, calcium chloride, or combinations thereof.

24. The process of claim 1, wherein the mole ratio of the aqueous base to the cholopropane ranges from 0.1 to 2.0.

25. The process of claim 1, wherein the process is a batch or continuous process.

26. The process of claim 1, wherein any one of the reaction steps are conducted in a jet stirred reactor or a series of jet stirred reactors.

27. The process of claim 1, wherein the process further comprises one or both of contacting the first crude chloropropene product with a chlorinating agent and contacting the second crude chloropropene product with a chlorinating agent.

28. A process for treating a chloropropane stream comprising reacting, in a first reaction, telogen, a metal containing catalyst, a promoter and a taxogen together to form a crude chloropropane product comprising a chloropropane and heavy byproducts;

splitting the crude chloropropane product into a light stream and a heavy stream, the light stream comprising the majority of the chloropropane, and the heavy stream comprising the remaining chloropropane, the heavy byproducts, the metal containing catalyst, the promoter, and any complexes formed from the promoter and metal containing catalyst;

contacting the heavy stream with an aqueous base in a second reaction to effect precipitation of the metal from the metal containing catalyst into an aqueous phase, and the formation of a first crude chloropropene product comprising chloropropene from a dehydrochlorination reaction;

separating the aqueous phase from the organic phase; and contacting the light fraction with a Lewis acid catalyst in a third reaction, thereby forming a second crude chloropropene product.

29. A system comprising:

a first reactor in which a mixture of a chlorinated methane, a metal containing catalyst, a promoter, and an alkene or vinyl chloride are reacted to form a crude chloropropane product comprising a chloropropane;

a separator in which the crude chloropropane product is separated into a light fraction and a heavy fraction, the light fraction comprising at least half of the chloropropane from the crude chloropropane, the heavy fraction comprising the remaining chloropropane and the metal containing catalyst, the promoter, and any complexes of the promoter and metal containing catalyst formed;

a second reactor in which the heavy fraction is contacted with an aqueous base thereby forming an aqueous phase comprising metal compounds precipitated from the metal containing catalyst and an organic phase comprising a first crude chloropropene product comprising chloropropene, the first crude chloropropene product formed via a dehyhdrochlorination reaction; and a third reactor in which the light fraction is contacted with a Lewis acid catalyst in a third reaction, thereby forming a second crude chloropropene product.

30. The system of claim 29, further comprising a second separator, in which the aqueous phase is separated from the organic phase.

31. The process of claim 1, wherein the process further comprises further purification of the first crude chloropropene product, the second crude chloropropene product or combinations thereof to remove byproducts formed in the dehydrochlorination reactions.

32. The process of claim 15, wherein the process further comprises one or both of contacting the first crude chloropropene product with a chlorinating agent and contacting the second crude chloropropene product with a chlorinating agent.

* * * * *